United States Patent
Ahmed et al.

(10) Patent No.: US 6,906,131 B2
(45) Date of Patent: Jun. 14, 2005

(54) CELLULOSE MATERIAL WITH IMPROVED ABSORBENCY

(75) Inventors: Iqbal Ahmed, Greensboro, NC (US); Angela Marie Jones, Greensboro, NC (US); Scott J. Smith, Greensboro, NC (US)

(73) Assignee: Stockhausen GmbH & Co. KG, Krefeld (DE)

( * ) Notice: Subject to any disclaimer, the term of this patent is extended or adjusted under 35 U.S.C. 154(b) by 71 days.

(21) Appl. No.: 09/954,348

(22) Filed: Sep. 17, 2001

(65) Prior Publication Data

US 2003/0055133 A1 Mar. 20, 2003

(51) Int. Cl.$^7$ .......... C08L 31/00; C08L 33/00; C08L 35/00
(52) U.S. Cl. .......... 524/832; 524/13; 524/35; 524/819; 524/827
(58) Field of Search .......... 524/35, 36–46, 524/819, 827, 832, 13

(56) References Cited

U.S. PATENT DOCUMENTS

| | | | |
|---|---|---|---|
| 4,410,571 A | 10/1983 | Korpman | |
| 4,444,830 A | 4/1984 | Erickson | |
| 4,727,097 A | * 2/1988 | Kabayashi et al. | 523/408 |
| 4,962,172 A | 10/1990 | Allen et al. | |
| 4,986,882 A | 1/1991 | Mackey et al. | |
| 5,160,789 A | 11/1992 | Barcus et al. | |
| 5,589,256 A | 12/1996 | Hansen et al. | |
| 6,270,893 B1 | 8/2001 | Young, Sr. et al. | |

FOREIGN PATENT DOCUMENTS

| | | |
|---|---|---|
| EP | 0 396 920 A1 | 11/1990 |
| EP | 0 676 496 A2 | 3/1995 |
| WO | WO 99/49905 | 10/1999 |

OTHER PUBLICATIONS

"Cellulose, Structure, Accessibility & Reactivity", Krassig, Hans A. p. 258.*
Fumihiko Onabe, Studies on Interfacial Properties of Polyelectrolyte—Cellulose Systems. I. Formation and Structure of Adsorbed Layers of Cationic Polyelectrolyte—(Poly–D-MDAAC) on Cellulose Fibers, Journal of Applied Polymer Science, vol. 22, pp. 3495–3510 (1978) Tokyo, Japan.

* cited by examiner

Primary Examiner—James J. Seidleck
Assistant Examiner—U. K Rajguru
(74) Attorney, Agent, or Firm—Smith Moore LLP

(57) ABSTRACT

An absorbent cellulose material having an application of superabsorbent polymer adhered to the cellulose material. In particular, the cellulose material has an application of pre-superabsorbent polymer adhered to the material, wherein an aqueous solution of pre-superabsorbent polymer is applied to the cellulose material and converted to superabsorbent polymer upon subjected to heat for a sufficient time. The absorbent cellulose material has a fluid retention of greater then 2g/g.

14 Claims, No Drawings

CELLULOSE MATERIAL WITH IMPROVED ABSORBENCY

TECHNICAL FIELD

The present invention relates to cellulose materials that have improved absorbency through the incorporation of polymers that absorb aqueous liquids (such as water, blood and urine). In particular, the invention relates to cellulose material treated with a pre-superabsorbent polymer that is converted to superabsorbent polymer upon heating of the treated cellulose material. The resulting cellulose material has enhanced absorbency over non-treated cellulose material.

Definitions of Abbreviations

| Abbreviations | Definitions |
|---|---|
| X-linking | cross-linking |
| SAP | superabsorbent polymer, a polymer which absorbs over 10 times its weight in water |
| pre-SAP | a polymer which is not a SAP and which is capable upon heating of becoming a SAP |
| CRC | centrifuge retention capacity |
| g | gram |
| DMAEA | dimethylaminoethyl acrylate |
| PAA | poly acrylic acid |
| DN | degree of neutralization |

BACKGROUND OF THE INVENTION

The present invention involves cellulose material and superabsorbent polymers. Cellulose material and the art of manufacture of cellulose material are well known to those skilled in the art. For example, cellulose material and the process to manufacture are discussed in the book entitled "Handbook for Pulp and Paper Technologist" (Angus Wilde Publications Inc., 1992) by Gary A. Smook.

General background of the manufacture of superabsorbent polymers can be seen in the journal article, "Keeping Dry with Superabsorbent Polymers", Chemtech, (September, 1994) by Buchholz. This article contains an excellent discussion of the conventional methods for making superabsorbent polymers. Also mentioned are various uses of superabsorbent polymers such as in disposable diapers, in a sealing composite between concrete blocks that make up the wall of underwater tunnels, and in tapes for water blocking in fiber optic cables and power transmission cables.

More general background with respect to various superabsorbent polymers and their methods of manufacture can be seen in U.S. Pat. No. 5,229,466 (issued Jul. 20, 1993) to Brehm and Mertens; U.S. Pat. No. 5,408,019 (issued Apr. 18, 1995) to Mertens, Dahmen and Brehm; and U.S. Pat. No. 5,610,220 (issued Mar. 11, 1997) to Klimmek and Brehm, all of which patents are assigned to Chemische Fabrik Stockhausen GmbH.

Superabsorbent polymers have been used to coat absorbent fibers and drying the coated fibers as disclosed for example see U.S. Pat. No. 4,962,172 (Issued Oct. 9, 1990) to Allen et al; and U.S. Pat. No. 5,160,789 (issued Nov. 3, 1992) to Barcus et al. Cellulose fibers have a retention capacity or CRC of about less then 2g/g i.e. cellulose fibers are considered to be a non-absorbent fiber. Furthermore, coating fibers with a polymer solution generally adversely affects the fibers other properties such as wicking power and makes the fiber brittle.

Another approach of adhering SAP to fibers is by the graft polymerization techniques as disclosed in U.S. Pat. No. 4,986,882 (issued Jan. 22, 1991) to MacKey et at. This approach discloses processes for making highly absorbent tissues and towels by wet-laying pulps comprising particular polycarboxylate polymer-modified fibrous pulps such as mildly hydrolyzed methyl acrylate-graft softwood kraft pulps. Graft polymerization method is a complicated method that requires a multi-step purifying process to remove the homopolymer and unreacted monomers.

Forming an absorbed layer of polyelectolyte on cellulose fibers is disclosed in the article Studies on Interfacial Properties of Polyelectrolyte-Cellulose Systems, J. Applied Polymer Science, Volume 22, pages 3495–3510 (1978).

The disclosures of all the above-mentioned patents and published patent applications are incorporated by reference.

SUMMARY AND OBJECTS OF THE INVENTION

A need exists for a cellulose material having enhanced absorbency and a method to make such a cellulose material.

Therefore, the present invention provides a method for making a treated cellulose material having enhanced absorbency. The method comprises first preparing an aqueous solution of pre-superabsorbent polymer, which is formed from at least one monomer, where the pre-superabsorbent polymer is capable upon being subjected to heating of becoming a superabsorbent polymer. Then cellulose material is provided that may be pretreated with a treatment solution comprising an aqueous alkaline solution. Next, a slurry is formed made up of the aqueous solution of pre-superabsorbent polymer and the cellulose material. The slurry is then filtered and heat-treated to obtain a treated cellulose material having an enhanced absorbency.

Accordingly, it is an object of the present invention to provide a method of making for treated cellulose material including a superabsorbent polymer, wherein the preferred method results in treated cellulose material having enhanced absorbency.

In addition to the method, the present invention provides an absorbent cellulose material comprising a cellulose material having an application of superabsorbent polymer composition adhered to the cellulose material wherein an aqueous solution of pre-superabsorbent polymer is applied to the cellulose material and converted to absorbent polymer upon subjected to heat for a sufficient time wherein the absorbent cellulose material has a fluid retention of greater than 2g/g.

Furthermore, the present invention provides an absorbent product selected from the group consisting of, agricultural products, fiber optic cables, power cables, water blocking tapes, insulation, hygiene articles, feminine care products, sanitary napkins, tampons, adult incontinence items, baby diapers, paper towels, sealing composites for concrete blocks, bandages, surgical sponges, meat trays, and bath mats, wherein the absorbent product comprises an absorbent cellulose material comprising a cellulose material having an application of superabsorbent polymer composition adhered to the cellulose material wherein an aqueous solution of pre-superabsorbent polymer is applied to the cellulose material and converted to absorbent polymer upon subjected to heat for a sufficient time wherein the absorbent cellulose material has a fluid retention of greater than 2g/g.

DETAILED DESCRIPTION OF THE INVENTION

The present invention provides a method for making a treated cellulose material having enhanced absorbency. The method includes a first preparation of an aqueous solution of pre-superabsorbent polymer, which is formed from at least one monomer, where the pre-superabsorbent polymer is capable upon being subjected to heating in a later step of the method of becoming a superabsorbent polymer. Cellulose material is provided that may be pretreated with a treatment solution comprising an aqueous alkaline solution. Next, slurry is formed made up of the aqueous solution of pre-superabsorbent polymer and the cellulose material. The slurry is then filtered and heat-treated to obtain a treated cellulose material having an enhanced absorbency.

The first preparation of the method includes an aqueous solution of pre-superabsorbent polymer (pre-SAP). As long as the above-mentioned pre-SAP is capable upon heating at a sufficient time and at a sufficient temperature of becoming a SAP (preferably, the pre-SAP has functional groups that will, upon provision of a sufficient amount of heating for a sufficient time, X-link to convert the pre-SAP into a SAP), the SAP may be manufactured by any of the prior art polymerization processes for making the SAPs.

Preferably, the pre-SAP is water soluble, a solution polymerization process is employed to make the pre-SAP, and the SAPs made this way are called solution polymerization SAPs.

Additionally, it is contemplated that any of the prior art emulsion or suspension polymerization processes may be employed to make the SAP with the following condition. A surfactant would have to be present in order to emulsify the aqueous monomer solution in the oil phase prior to polymerization. Suitable surfactants for use in the present invention are well known to those of skill in the art of emulsion polymerization. The SAPs made this way are called emulsion polymerization SAPs.

Thus, by the term "aqueous solution" of the polymer (i.e., of the pre-SAP) is meant to include a true aqueous solution, as well as to include an aqueous suspension that has present in it a surfactant.

Thus, the SAP may be obtained by polymerizing at least about 10%, more preferably about 25%, even more preferably about 55 to about 99.9%, by weight of monomers having olefinically-unsaturated carboxylic and/or sulfonic acid groups. Such acid groups include, but are not limited to, acrylic acid, methacrylic acid, 2-acrylamido-2-methylpropane sulfonic acid, and mixtures thereof. The acid groups are present partially as salts, such as sodium, potassium, or ammonium salts.

The acid groups are typically neutralized to at least about 25 mol %, more preferably at least about 50 mol %. More particularly, the preferred SAP has been formed from X-linked acrylic acid or methacrylic acid, which has been neutralized to an extent of about 50 to about 80 mol %, more preferably about 60 to about 70 mol %. Suitable neutralizing agents are hydroxides and/or carbonates of alkaline earth metals and/or alkali metals, for instance, NaOH. Neutralization of acid groups may be performed prior to the polymerization to form the pre-SAP, may be performed on the pre-SAP, or a combination thereof.

Additional useful monomers for making the SAPs include from about 0 up to about 60% by weight of acrylamide, methacrylamide, maleic acid, maleic anhydride, esters (such as hydroxyethyl acrylate, hydroxypropyl acrylate, hydroxyethyl methacrylate, hydroxypropyl methacrylate, glycidyl methacrylate, dimethyl-aminoalkylacrylate, dimethyl-aminoalkyl-methacrylate, diethylaminoalkyl acrylate, diethylaminoalkyl methacrylate and tertairy butylaminoalkyl methacrylate), dimethyl-aminopropyl acrylamide, N,N-Dimethylacrylamide, N,N-Dimethylmethacrylamide, N,N-Diethylacrylamide, N,N-Diethylmethacrylamide, dimethyldiallylamine, 3-methacrylamidopropyldimethylamine, 2-methacrylamido-2-methylpropanedimethylamine, 2-methacrylamido-2-methylbutanedimethylamine, N-vinyl imidazole, 1-methyl-2-vinylimidazole, 2-vinylimidazole, 4(5)-vinylimidazole, 2-vinylpyridine, 4-vinylpyridine, and quaternary salts of monomeric amines. A preferred amount is from about 1% to about 55%, more preferably from about 2% to about 10% by weight. A suitable hydroxypropyl acrylate for use in the present invention is sold under the trade name Mhoromer AM 438 by Creanova, Inc. Such monomers may be present whether or not a network X-linking agent as described in the next paragraph, is present.

Suitable network X-linking agents that may be used in making the SAPs are those, which have 1 ethylenically unsaturated double bond and 1 functional group reactive toward acid groups, and those, which have several functional groups reactive toward acid groups. Very minor amounts of network X-linking agents which have at least 2 ethylenically unsaturated double bonds may also be used to enhance performance. Suitable kinds of network X-linking agents include, but are not limited to, acrylate and methacrylate of polyols (such as butanediol diacrylate, polyglycol diacrylate, hexanediol dimethacrylate, tetrahydrofurfury-2-methacrylate, glycerol dimethacrylate, trimethylolpropane triacrylate, allyloxy polyethylene glycol methacrylate, and ethoxylated trimethylolpropane triacrylate), allyl acrylate, diallyl acrylamide, triallyl amine, diallyl ether, N-methylol acrylamide, methylenebisacrylamide, glycerol dimethacrylate, N,N-dimethylaminoethyl methacrylate, N-dimethylaminopropyl methacryladmide, and N-methylol methacrylamide, two or more valent metal, diglycidyl ether, diamine, halohydrin, polyisocyanate, dihaloalkane, polyfunctional aziridine compound, dialdehyde, disulfonate ester, multi-functional acid halide, organic carbonate and mixtures thereof.

The diglycidyl ether is very suitable for use in the present invention and is sold under the trade name: DENACOL®EX830 by Nagase Chemicals Ltd. In the embodiment where one or more of these network X-linking agents is not employed then one or more of the monomers noted in the previous paragraph may effect network X-linking.

In the preferred embodiment of the invention, the SAP is formed by heating the pre-SAP in the last step of the method.

More preferably, heating may be conducted in the presence of a diglycidyl ether as a network X-linking agent, which causes functional groups, such as hydroxyl and/or carboxyl present in the pre-SAP to X-link via epoxy groups of X-linking agent and form the SAP. A typical temperature range for the network X-linking to convert the pre-SAP into a SAP is selected based on the equipment and process conditions and may range from about 60° C. to about 140° C., more preferably from about 110 to about 135° C. and most preferably from about 120 to about 130° C.

In the event where no network X-linking agents is employed and one or more of the monomers noted in the previous paragraph effecting network X-linking, the heating to convert the pre-SAP into the SAP may require a higher temperature.

Regardless of whether a network X-linking agent, as defined herein, is present or not, the time for heating typically is from about 30 seconds to about 60 minutes. A time of about 1 to about 50 minutes is very typical. The specific time and temperature are not critical, as long as they are sufficient to X-link the pre-SAP and convert it into a SAP.

Cellulose materials used in the present invention, such as cellulose fibers, are commercial products available from various manufacturers such as Georgia Pacific, Rayonier, etc. The cellulose materials may be used by itself with the aqueous solution of the pre-SAP or in the form of a pre-treated aqueous cellulose form. A pre-treated aqueous cellulose is formed by pre-treating a cellulose material with a treatment solution comprising aqueous alkaline solution. A suitable aqueous alkaline solution is NaOH, preferably in the concentration of about 0.5N. The treated cellulose fiber is filtered and washed and optionally dried.

In an example procedure, about 30 grams of commercial cellulose pulp was stirred in 1.5 liter of 0.5 N NaOH solution at room temperature for 1.5 hours. The pulp fiber was then filtered and thoroughly washed in a funnel until the effluent reached pH of 7. The fiber was finally washed with de-ionized water. The wet fiber was air dried in the hood first followed by drying in an oven at 60° C.

Next, a slurry is formed made up of the aqueous solution of pre-superabsorbent polymer and the pre-treated aqueous cellulose. The slurry is agitated for a sufficient amount of time, then filtered and heat-treated to obtain a treated cellulose material having an enhanced absorbency.

For example to illustrate the preparation of the slurry, about 100 milliliters of approximately 1.5% polymer solution was prepared by diluting the appropriate amount of pre-superabsorbent polymer. One gram of freshly prepared 0.23% DENACOL®EX830 (Nagase Chemicals Ltd., Nishi-Ku, Osaka Japan, a polyethylene glycol diglycidyl ether was added to the dilute polymer solution. The mixture was vigorously stirred at room temperature. About 1 gram of dry pre-treated pulp cellulose fiber made in cellulose pre-treatment step was added to the polymer solution. The mixture was stirred at room temperature for 6 hours. The wet pulp was then filtered and allowed to air dry at room temperature. The cellulose fiber was then heated at 120° C. for 30 minutes. The resulting pulp cellulose fiber was shredded in a blender to make a fluff. The fluffed cellulose fiber was then sieved with 100-mesh size screen to remove fine fiber particles.

In addition to the foregoing steps superabsorbent polymer fines can be added to the process to enhance the absorbency of the cellulose material. SAP fines are commercially available from Stockhausen under the trademark FAVOR®SAP fines. The SAP fines are added to the slurry preparation. For example, an aliquot of SAP fines may be added to the fiber slurry and/or to the aqueous solution of the pre-SAP. The SAP fines are vigorously stirred into the slurry or the aqueous solution for a few minutes to yield a homogeneous mixture.

In addition to the foregoing it is recognized that the present invention can be used in the manufacture of pulp and paper or the manufacture of cellulose material. In particular, the present invention can be used as a part of the manufacturing process that is in line with current pulp, paper and cellulose material manufacturing techniques.

Various end use absorbent products that may contain the cellulose material having enhanced absorbency of the present invention include, but are not limited to, agricultural products (i.e., a polymer with herbicide and/or insecticide), fiber optic cables, power cables, water blocking tapes, insulation, hygiene articles, feminine care products (i.e., sanitary napkins and/or tampons), incontinence items for adults, diapers for babies, paper towels, sealing composites between concrete blocks, bandages, surgical sponges, meat trays, bath mats, and the like.

To characterize the SAPs as set out in the Laboratory Examples below the centrifuge retention capacity (CRC) were measured in the following manner.

CRC Test. The test was conducted at ambient conditions of room temperature. Retention of 0.9% saline solution was determined according to the tea bag test method and reported as an average value of 2 measurements. Approximately 100 mg of Cellulosic material particles, were enclosed in a tea bag and immersed in the saline solution for 30 minutes. Next individually hang each teabag up by the corners to drip-dry for 10 minutes. Then, the tea bag was centrifuged at 1400 rpm for 5 minutes and weighed. The diameter of the centrifuge apparatus was about 21 cm. Also, 2 tea bags without particles were used as blanks.

The specific procedure is as follows:

1. Cut the teabag stock into 3×5-inch rectangles. Fold the strips in half, and seal two of the three open sides so the inside edge of the seals are about ¼ inch from the edge of the teabag.
2. For each determination, weigh 0.100+/−0.005 grams of modified cellulosic material into a teabag. Record the initial weight as $W_1$.
3. Seal the open side of the teabags using the heat sealer. Store the teabags in a desiccator if the period of time between the initial weighing and the determination is greater than 30 minutes.
4. Prepare the two test method blanks by heat-treating two empty teabags without cellulose material sample.
5. Fill a dish with 0.9% saline solution to approximately 4 cm high.
6. Prepare the sealed teabags for immersion by gently shaking the sample to distribute the cellulosic material evenly across the teabag.
7. Immerse the teabags in the 0.9% saline.
8. After 30 minutes, remove the teabags from the test liquid.
9. Individually hang each teabag up by the corners to drip-dry for 10 minutes.
10. Place the teabags into the centrifuge making sure to balance the centrifuge with proper teabag placement. Centrifuge for 3 minutes at 1600 rpm.
11. After centrifugation, determine the weights of each sample. Record the weights of the test blanks, without test sample (W2) and the weight of the teabag with test sample accurate to 0.01($W_3$).

Then, the CRC property (measured in grams of liquid absorbed per gram of particles) was calculated according to the following equation.

$$CRC = (W_3 - W_2 - W_1)/W_1$$

where:

CRC=retention after 30 minutes immersion time (g/g)

$W_1$=initial weight in grams of SAP particles $W_2$=average weight in grams of two blanks after centrifugation $W_3$=weight in grams of test tea bag after centrifugation

EXAMPLES 1–5

Outline of Procedure

A method of making the cellulose material of the present invention follows the following general procedure:

Step 1—Preparation of Pre-superabsorbent Polymer

An aqueous acrylic acid solution (50 grams acrylic acid in 374.91 grams of water) comprising approximately 3 mole percentage dimethylaminoethyl acrylate, relative to acrylic acid was neutralized with sodium hydroxide (NaOH) solution under cooling condition. The degree of neutralization amounted to about 50 mole percentage and the total monomer concentration amounted to 10 weight %. 500 gram of monomer solution was cooled to 10° C. and purged with nitrogen for 5 minutes. Subsequently, 10 gram of 1 weight % $H_2O_2$, 19.90 gram of 2.01 weight % sodium pensulfate, 4.41 gram of 2.27% azo bis-2-amidino propane dihydrochloride and 10 gram of 0.5 weight % of sodium erythorbate were added. If polymerization does not begin within 5 minutes, a few drops of an aqueous $FeSO_4$ is added to kick off the reaction which could be recognized by rapid rising of temperature of the monomer solution. The monomer solution became a very viscous solution after about 2 hours and the resulting viscous polymer solution was allowed to cool down to room temperature before it was ready to be used.

Step 2—Preparation of Cellulose Fiber

About 30 grams of commercial cellulose fiber was stirred in 1.5 liter of 0.5 N NaOH solution at room temperature for 1.5 hours. The cellulosic fiber was then filtered and thoroughly washed in a funnel until the effluent reached a pH of 7. The fiber was finally washed with de-ionized water. The wet fiber was air dried in the hood first followed by drying in an oven at 60° C.

Step 3—Preparation of Slurry.

About 100 milliliters of approximately 1.5% polymer solution was prepared by diluting the appropriate amount of pre-superabsorbent polymer prepared in Step 1. One gram of freshly prepared 0.23% DENACOL®830 (Nagase Chemicals Ltd., Nishi-Ku, Osaka Japan0, a polyethylene glycol diglycidyl ether was added to the dilute polymer solution. The mixture was vigorously stirred at room temperature. About 1 gram of dry pre-treated pulp cellulose fiber made in Step 2 was added to the polymer solution and the resulting slurry was stirred for several hours. The slurry was then filtered and the wet pulp was then allowed to air dry at room temperature. The cellulose fiber was then heated at 120° C.—for 30 minutes. The resulting pulp cellulose fiber was shredded in a blender to make a fluff. The fluffed cellulose fiber was then sieved with 100-mesh size screen to remove fine fiber particles.

| Sample | Treatment | Process | Fluid Retention (g/g) |
|---|---|---|---|
| Control | Cellulose fiber | | 1.5–2.0 |
| 1 | Cellulose fiber treated with DMAEA containing 50% DN PAA solution (1.5%) & 0.16% DENACOL ® EX830. | Stirred 6 hours, vacuum filtered, dried at room temperature then heated at 120° C./10 min, shredded & fluffed by a blender | 3.2 |
| 2 | Alkali treated cellulose fiber treated with DMAEA containing 50% DN PAA solution (2%) & 0.16% DENACOL ® EX830. | Stirred 6 hours, vacuum filtered, dried at room temperature then heated at 120° C./10 min, shredded & fluffed by a blender. | 4.1 |
| 3 | Alkali treated cellulose fiber with DMAEA containing 50% DN PAA solution (1.5%) & 0.16% DENACOL ® EX830. | Stirred 6 hours, vacuum filtered, dried at room temperature then heated at 120° C./10 min, shredded & fluffed by a blender. | 4.9 |
| 4 | Alkali treated cellulose fiber treated with NaOH treated cellulosic material fluff treated with 50% DN PAA solution (1.37%) & 0.2% DENACOL ® EX830 | Stirred 6 hours, vacuum filtered, dried at room temperature then heated at 120° C./10 min, shredded & fluffed by a blender. | 4.9 |
| 5 | Alkali treated cellulose fiber treated with DMAEA containing 50% DN PAA solution (1.6%) & 0.2% DENACOL ® EX830 | Stirred 6 hours, vacuum filtered, dried at room temperature then heated at 120° C./10 min, shredded & fluffed by a blender. | 5.8 |

EXAMPLES 6–13

Outline of Procedure

Another method of making the cellulose material of the present invention follows the following general procedure:

Step 1—Preparation of Pre-Superabsorbent Polymer

An aqueous acrylic acid solution (50 grams acrylic acid in 374.91 grams of water) comprising approximately 3 mole percentage dimethylaminoethyl acrylate, relative to acrylic acid was neutralized with sodium hydroxide (NaOH) solution under cooling condition. The degree of neutralization amounted to about 50 mole percentage and the total monomer concentration amounted to 10 weight %. 500 gram of monomer solution was cooled to 10C.° and purged with nitrogen for 5 minutes. Subsequently, 10 gram of 1 weight % $H_2O_2$, 19.90 gram of 2.01 weight % sodium pensulfate, 4.41 gram of 2.27% azo bis-2-amidino propane dihydrochloride and 10 gram of 0.5 weight % of sodium erythorbate were added. If polymerization does not begin within 5 minutes, a few drops an aqueous $FeSO_4$ is added to kick off the reaction which could be recognized by rapid rising of temperature of the monomer solution. The monomer solution became a very viscous solution after about 2 hours and the resulting viscous polymer solution was allowed to cool down to room temperature before it was ready to be used.

Step 2—Preparation of Cellulose Fiber

About 30 grams of commercial cellulose fiber was stirred in 1.5 liter of 0.5 N NaOH solution at room temperature for 1.5 hours. The cellulose fiber was then filtered and thoroughly washed in a funnel until the effluent reached ph of 7. The fiber was finally washed with de-ionized water. The wet fiber was air dried in the hood first followed by drying in an oven at 60° C.

Step 3—Preparation of Slurry.

About 198 milliliters of approximately 1.5% polymer solution was prepared by diluting the appropriate amount of pre-superabsorbent polymer prepared in Step 1. One gram of freshly prepared 0.23% DENACOL®830 (Nagase Chemicals Ltd., Nishi-Ku, Osaka Japan0, an polyethylene glycol diglycidyl ether was added to the dilute polymer solution. The mixture was vigorously stirred at room temperature. About 2 gram of dry pre-treated cellulose fiber made in Step 2 was added to the polymer solution and stirred for some time to obtain an uniform slurry. An aliquot of pre-surface cross-linked SAP fines were added to the fiber slurry and was vigorously stirred for a few minutes to yield a homogeneous mixture. The fiber/SAP slurry was then filtered under vacuum (30 inches Hg). The wet pulp was then allowed to air dry at room temperature. The cellulose fiber was then heated at 120° C.—for 30 minutes. The resulting pulp cellulose fiber was shredded in a blender to make a fluff. The fluffed cellulose fiber was then sieved with 100-mesh size screen to remove fine fiber particles.

| Sample | Cellulose Fiber/SAP Fines Composition | Process | Fluid Retention (g/g) |
|---|---|---|---|
| Control | Cellulose fiber as received | | 1.5–2.0 |
| 6 | 2 gram of cellulose fiber as received; 198 g 1.5% copolymer solution of 50% DN PAA & DMAEA & 2 g of 0.5186% DENACOL EX830 & 1 g FAVOR ® SAP fines. | First, the cellulose fiber was stirred in polymer/crosslinker solution mixture for an hour to obtain an uniform slurry; then SAP fines were added and mixed well and immediateley filtered under vacuum. The pad thus obtained was dried at 120° C. | 7.1 |
| 7 | 2 gram of cellulose fiber as received; 198 g 1.5% copolymer solution of 50% DN PAA & DMAEA & 2 g of 0.5186% DENACOL EX830 & 1 g FAVOR ® SAP fines. | First, SAP fines were stirred in polymer/crosslinker solution mixture to obtain an uniform slurry; then cellulose fiber was added and stirred well to obtain an uniform mixture. The mixture was then filtered under vacuum. The pad thus obtained was dried at 120° C. | 7.3 |
| 8 | 2 gram of dried alkali treated cellulosic; 198 g 1.44% copolymer solution of 50% DN PAA & DMAEA & 2 g of 0.5186% DENACOL EX830 & 1 g FAVOR ® SAP fines. | First, the cellulose fiber was stirred in polymer/crosslinker solution mixture for an hour to obtain an uniform slurry; then SAP fines were added and mixed well and immediately filtered under vacuum. The pad thus obtained was dried at 120° C. | 6.3 |
| 9 | 2 gram of dried alkali treated cellulose fiber; filtrate from Example 8 & 1 g FAVOR ® SAP fines | The filtrate was refiltered, made slurry with fiber, then SAP fines were added, mixed well, filtered and dried the resulting pad at 120° C. | 7.3 |
| 10 | 2 gram of dried alkali treated cellulose fiber; 198 g 1.44% copolymer solution of 50% DN PAA & DMAEA & 2 g of 0.5186% DENACOL EX830 & 1 g FAVOR ® SAP fines | First, cellulose fiber was stirred in polymer/crosslinker solution mixture for an hour to obtain an uniform slurry; then SAP fines were added and mixed well and immediately filtered under vacuum. The pad thus obtained was dried at 120° C. | 7.1 |
| 11 | 2 gram of dried alkali cellulose fluff, 198 g 1.44% copolymer solution of 50% DN PAA & DMAEA & 2 g of 0.5186% DENACOL EX830 & 1 g FAVOR ® SAP fines | First cellulose fluff was stirred in polymer/crosslinker solution mixture for an hour to obtain an uniform slurry; then SAP fines were added and mixed well and immediately filtered under vacuum. The pad thus obtained was dried at 120° C. | 8.3 |
| 12 | 2 gram of dried alkali cellulose fiber, filtrate from Example 10 & 1 g FAVOR ® SAP fines. | The filtrate refiltered, made slurry with fiber, then SAP fines add, mixed well, filtered, and dried the resulting pad at 120° C. | 8.5 |
| 13 | 2 gram of alkali cellulose fiber, 35 g 1.44% copolymer solution of 50% DN PAA & DMAEA & 2g of 0.5186% DENACOL EX830 & 1 g FAVOR ® SAP fines | First, cellulose fluff was mixed with 25 g of polymer/crosslinker solution, then the paste like mixture was transferred to a blender and 1 g of SAP fines was added. The content was blended at a low speed for a couple of minutes. Then an additional 10 g of polymer/crosslinker solution was added to the blender and the whole content was blended at a high speed for 2–3 minutes. The paste was then vacuum filtered to remove excess fluid (~5 g). The pad thus obtained was dried at 120° C. | 9.6 |

It will be understood that various details of the invention may be changed without departing from the scope of the invention. Furthermore, the foregoing description is for the purpose of illustration only, and not for the purpose of limitation of the invention being defined by the claims.

What is claimed is:

1. A method for making a treated cellulose material having enhanced absorbency, said method comprising
   (a) preparing an aqueous solution of pre-superabsorbent polymer, which is formed from at least one monomer, and wherein the pre-superabsorbent polymer has functional groups attached thereto, where the functional groups of the pre-superabsorbent polymer upon heating will crosslink to convert the pre-superabsorbent polymer to a superabsorbent polymer;
   (b) providing cellulose material;
   (c) preparing a slurry comprising the aqueous solution of pre-superabsorbent polymer and cellulose material;
   (d) filtering and heat treating the slurry to obtain a treated cellulose material having enhanced absorbency.

2. The method of claim 1 wherein pre-superabsorbent is a water soluble polymer.

3. The method of claim 1 wherein the pre-superabsorbent polymer is formed from a monomer selected from the group consisting of carboxylic acid monomer, salt of carboxylic acid monomer, nitrogen containing vinylic monomer, and hydroxyl monomer.

4. The method of claim 1 wherein a network crosslinking agent is added to the aqueous solution of pre-superabsorbent polymer and the functional groups of the pre-superabsorbent polymer include hydroxyl and/or carboxyl groups.

5. The method of claim 1 wherein the crosslinking agent is diglycidyl ether.

6. The method of claim 1 wherein the cellulose material of step (b) is pretreated with an aqueous alkali solution.

7. The method of claim 1 wherein the cellulose material is cellulose fiber.

8. A method for making a treated cellulose material having enhanced absorbency, said method comprising
   (a) preparing an aqueous solution of pre-superabsorbent polymer, which is form from at least one monomer, where the pre-superabsorbent polymer is capable upon being subjected to heating of becoming a superabsorbent polymer;
   (b) providing cellulose material;
   (c) providing superabsorbent polymer fines;

(d) preparing a slurry comprising the aqueous solution of pre-superabsorbent polymer, the superabsorbent polymer fines, and the cellulose material; and (e) filtering and heat treating the cellulose material to convert the aqueous solution of pre-superabsorbent and superabsorbent polymer fines into a superabsorbent polymer resulting in a treated cellulose material having enhanced absorbency.

9. The method of claim 8 wherein a network crosslinking agent is added to the aqueous solution of pre-superabsorbent polymer.

10. The method of claim 8 wherein the cellulose material of step (b) is pretreated with an aqueous alkali solution.

11. The method of claim 8 wherein the cellulose material is cellulose fiber.

12. The method of claim 8 wherein pre-superabsorbent is a water soluble polymer.

13. The method of claim 8 wherein the pre-superabsorbent polymer is formed from a monomer selected from the group consisting of carboxylic acid monomer, salt of carboxylic acid monomer, nitrogen containing vinylic monomer, and hydroxy monomer.

14. The method of claim 8 wherein the aqueous alkaline material is sodium hydroxide.

* * * * *

UNITED STATES PATENT AND TRADEMARK OFFICE
CERTIFICATE OF CORRECTION

PATENT NO. : 6,906,131 B2 Page 1 of 1
DATED : June 14, 2005
INVENTOR(S) : Iqbal Ahmed, Angela Marie Jones and Scott J. Smith It is certified that error appears in the above-identified patent and that said Letters Patent is hereby corrected as shown below:

<u>Title page,</u>
Item [57], ABSTRACT,
Line 7, "upon subjected" should read -- upon being subjected --.
Line 9, "then" should read -- than --.

<u>Column 2,</u>
Line 1, "fibers" should read -- fibers' --.
Line 5, "et at." should read -- et al. --.
Line 45, -- being -- should be inserted after "upon".

<u>Column 3,</u>
Line 34, please delete the word "by".

<u>Column 6,</u>
Line 50, "3 minutes at 1600 rpm" should read -- 5 minutes at 1400 rpm --.

<u>Column 7,</u>
Line 38, "Osaka Japan0" should read -- Osaka Japan) --.

<u>Column 8,</u>
Line 61, "Osaka Japan0" should read -- Osaka Japan) --.

<u>Column 10,</u>
Line 62, "form" should read -- formed --.

Signed and Sealed this

Twenty-second Day of November, 2005

JON W. DUDAS
*Director of the United States Patent and Trademark Office*